United States Patent [19]
Muller et al.

[11] Patent Number: 5,544,219
[45] Date of Patent: Aug. 6, 1996

[54] PROCEDURE FOR AUTOMATIC POSITION-FINDING OF POINTS OF INTEREST DURING A MAMMOGRAPHY EXAMINATION USING STEREOTACTIC TECHNIQUE

[75] Inventors: Serge Muller, Guyancourt; Michel Grimaud, Paris; Robert Heidsieck, Chesnay, all of France

[73] Assignee: GE Medical Systems, Buc, France

[21] Appl. No.: 332,743

[22] Filed: Nov. 1, 1994

[30] Foreign Application Priority Data

Nov. 9, 1993 [FR] France ................................ 93 13323

[51] Int. Cl.⁶ .......................................... A61B 6/12
[52] U.S. Cl. ........................... 378/210; 378/98.12
[58] Field of Search ................... 364/413.13, 413.23; 378/62, 98, 98.2, 98.7, 98.8, 98.12, 37, 41, 42, 210

[56] References Cited

U.S. PATENT DOCUMENTS

| | | |
|---|---|---|
| 5,058,177 | 10/1991 | Chemaly . |
| 5,164,993 | 11/1992 | Capozzi et al. ................... 378/98.8 |
| 5,262,945 | 11/1993 | DeCarli et al. ................... 364/413.13 |
| 5,287,546 | 2/1994 | Tesic et al. ................... 378/54 |
| 5,426,684 | 6/1995 | Gaborski et al. ................... 378/62 |

FOREIGN PATENT DOCUMENTS

WO92/21093  11/1992  WIPO .
WO93/11706  6/1993  WIPO .

*Primary Examiner*—David P. Porta
*Attorney, Agent, or Firm*—Pollock, Vande Sande & Priddy

[57] ABSTRACT

A process is disclosed which involves automatic position-finding for a point of interest of an object that exhibits high contrast as compared with surrounding tissues, the process being carried out by means of a stereotactic photographic device that includes a digital image acquisition system. The process includes a number of steps for each image belonging to the pair of stereotactic images. An initial analysis of a histogram of the image pixels are made, and a subsequent determination is made of a threshold corresponding to the difference between the high contrast objects and the surrounding tissues. A subsequent determination is made of the threshold of the image, in order to obtain a binary image incorporating two gray levels. This is followed by the filtering of the threshold determined image in the preceding step, based on morphological criteria of the object in which the point of interest is located. This operation is designed to obtain a segmented projection of the object of interest. This is followed by the localization of the point of interest in the image reference mark. Utilization of the process is for stereotactic examinations performed during mammography.

6 Claims, 8 Drawing Sheets

PROCEDURE FOR AUTOMATIC POSITION-FINDING OF POINTS OF INTEREST DURING A MAMMOGRAPHY EXAMINATION USING STEREOTACTIC TECHNIQUE

The present invention concerns a procedure for automatic position-finding of points of interest encountered during a mammography examination using stereotactic technique, which is performed by a stereotactic photographic device comprising a digital image-acquisition system associated with image-processing algorithms. A procedure of this kind is used most especially in the medical field, where mammography entails an examination making it possible to detect breast tumors and to carry out medical and surgical treatment.

An examination utilizing stereotactic techniques normally makes it possible to gain access with a high degree of accuracy (to within about 1 millimeter) to a given point of a three-dimensional object, based on two-dimensional projections of this object made according to two opposite, angled incidences on either side of the perpendicular to the plane of the image receiver delivering these projections.

From knowledge, first, of the position of the projection of the given point in the plane of each projection, and second, of the geometry underlying the construction of the two projections, it becomes possible to calculate the exact position of this point in three-dimensional space by trigonometric calculation. In the field of mammography, the stereotactic examination makes it possible to access with precision a given point in the volume of the breast being examined, and to accurately position a needle in the breast. It then becomes clinically possible either to perform a cytopuncture or a microbiopsy, in order to analyze histologically the cells collected as a specimen, or to perform position-finding prior to surgery by marking out an area within the breast with a dye, a carbon-containing compound, or a metallic marker, otherwise called a "fish hook."

Currently, in the field of mammography, stereotactic examinations are performed using a mammographic machine equipped with a stereotactic photographic device. The mammography machine incorporates an X-ray tube located at the end of a first arm which moves around an axis and which emits X-rays toward a receiver positioned at the end of the other arm. Between the tube and receiver are arranged a breast-support plate, otherwise known as a patient support, and a compression plate which holds the breast in place during mammography. The image receiver is either a photographic film or a digital receiver (e.g., a CCD camera). Stereotactic photography requires rotation of the X-ray tube around the breast-support and compression plates according to two successive, opposite directions on either side of its initial position perpendicular to the plane of the image receiver. In practice, therefore, the stereotactic mammography examination consists of the following steps:

after positioning and compressing the breast, a first exposure is made according to an incidence orthogonal to the plane of the image receiver, this exposure then being used as the reference for the angles. This step makes it possible to verify that the point of interest to which access is desired within the breast is present in the field of view of the receiver;

a second exposure is taken at an angular incidence of +0, then a third exposure at an angular incidence of −0, 0 being typically 15 degrees in relation to the reference incidence.

The radiologist must, using two cursors on the two stereotactic exposures, first, locate the two homologous points corresponding to the physical location of the lesion the radiologist wishes to reach in the breast with the tip of the needle; and second, the two homologous points corresponding to the physical reference point of the coordinates of the needle positioner, also termed the needle-carrier. Once the x and y coordinates of these four points in the plane of the receiver have been located, a digital computer first determines the x, y, and z coordinates in the space of the point of the lesion and of the needle-carrier reference, and, knowing the size of the needle and the geometry of acquisition system, the computer then indicates to the radiologist the gap between the current position of the needle-carrier and the reference position of this needle-carrier, which should enable the needle to reach the point of interest of the lesion. The radiologist then cancels out the gaps $\delta x$, $\delta y$, and $\delta z$ by operating the wheels actuating the needle-positioning device along the three axes x, y, and z, so that, by placing the needle along these axes, it can reach the target point of the lesion. Finally, during a control procedure, the radiologist verifies that the tip of the needle is indeed positioned in the breast, by taking once again two photographic exposures at an incidence of +/−0, before performing the puncture or marking operation.

This radiological examination has the disadvantage of being relatively long and painful for the patient. Accordingly, the present invention is intended to reduce the length of the stereotactic examination, by reducing the number of operations performed by the radiologist, while at the same time increasing examination accuracy.

To this end, the invention utilizes as an image receiver, instead of the traditional photographic film, a digital image-acquisition system associated with image-processing algorithms emitted by this system, in order to automate the position-finding of four points of interest.

These four points of interest include:

the two homologous points corresponding to the physical point of reference of the needle-carrier, the two homologous points corresponding to the tip of the needle on the two control stereoscopic exposures.

A first object of the invention is a procedure for automatic position-finding of a point of interest of an object shown in high contrast in relation to the surrounding tissues by means of a stereotactic photographic device comprising a digital image-acquisition system associated with algorithms for processing these images, this procedure being characterized by the fact that it comprises the following steps, for each image belonging to the pair of stereotactic images:

1) analysis of the histogram of the pixels belonging to the image and determination of a threshold corresponding to the difference between the highly-contrasted objects and the surrounding tissues;

2) determination of the threshold of the image so as to produce a binary image incorporating two gray levels;

3) filtering of the image for which the threshold was determined in the preceding step using the morphological criteria of the object where the point of interest is found, this filtering operation being designed to obtain the segmented projection of the object of interest;

4) localization of the point of interest in the image reference mark.

Other features and advantages of the invention will emerge from a reading of the following description of a specific embodiment of the procedure, this description being provided with respect to the attached drawings, in which:

The elements bearing the same references in these various figures perform the same functions for the purpose of achieving the same results.

Figure 1:
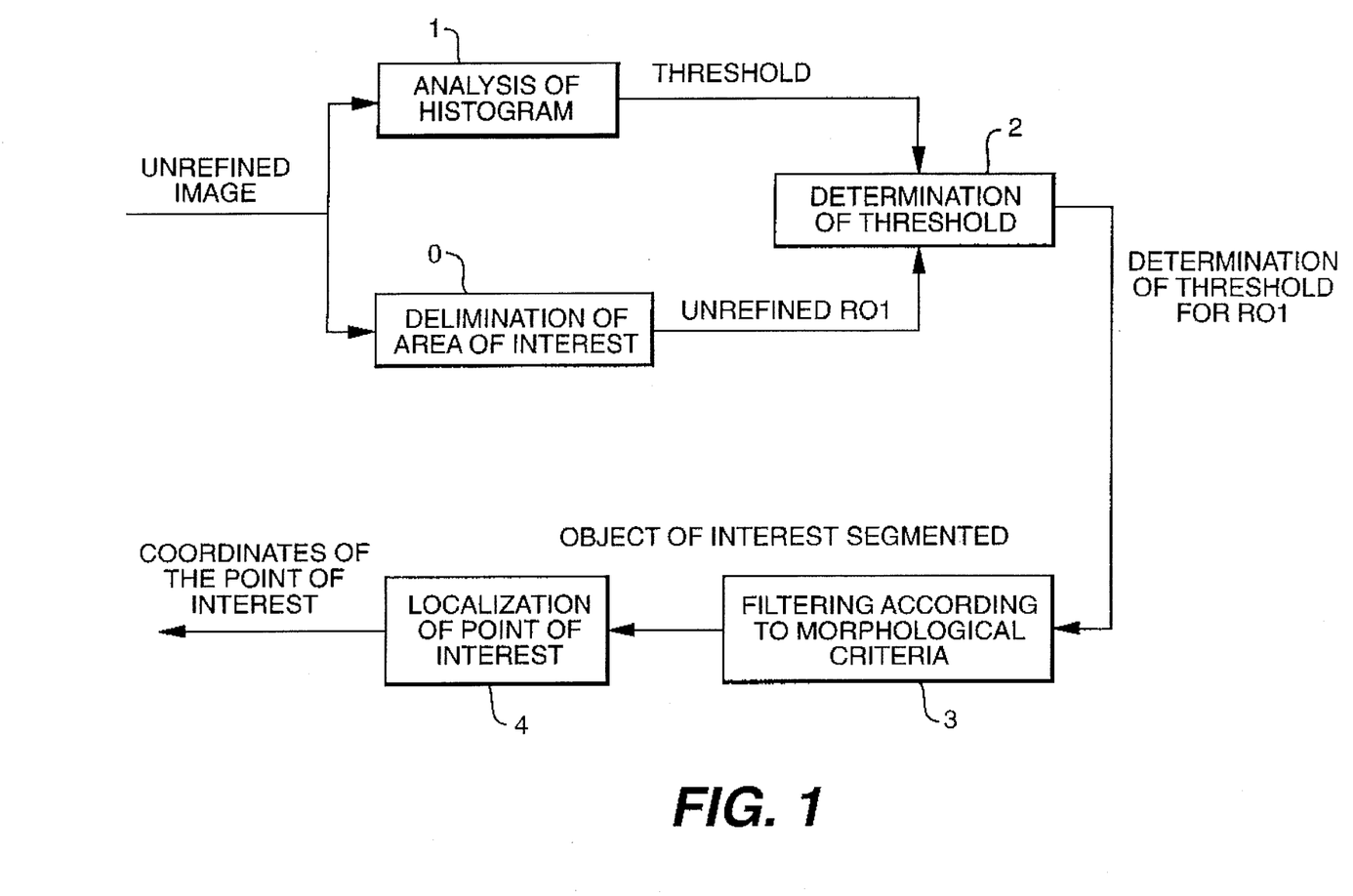
FIG. 1 is the block-diagram of the position-finding procedure according to the invention.

The block diagram in FIG. 1 shows the different steps in the procedure for automatic position-finding of the homologous points corresponding to the physical origin of the coordinates of the needle-carrier, this origin being, for example, the center of a cross when a STEREOTIX device is used. This procedure also makes it possible to locate the two homologous points on the two stereotactic control images. These four points belong to objects exhibiting high contrast in relation to tissues of the surrounding mammary gland. The procedure will be described as it relates to detection of the point of reference of the needle-carrier, but it applies in an identical way to detection of the needle tip.

Because of the knowledge of the geometry of the system of acquisition and of the dimensions of the components of the stereotactic photographic system, i.e., the distance between the focal point of the X-ray tube and the image receiver, the angle formed by the column supporting the tube and the line perpendicular to the image receiver, the relative position of the needle-carrier with the patient-support, for example, step 0 consists in delimiting on one of the two unrefined images (illustrated in FIG. 2a) of the pair of stereoscopic images an area of interest containing the projection of the object on which the point of reference is found, this object being the cross formed by the patient-support in the example described.

This step, although not mandatory for carrying out the procedure, has the advantage of reducing calculations, since it makes possible the treatment, not of the entire image, but only of the interior of an area.

Figure 2A:
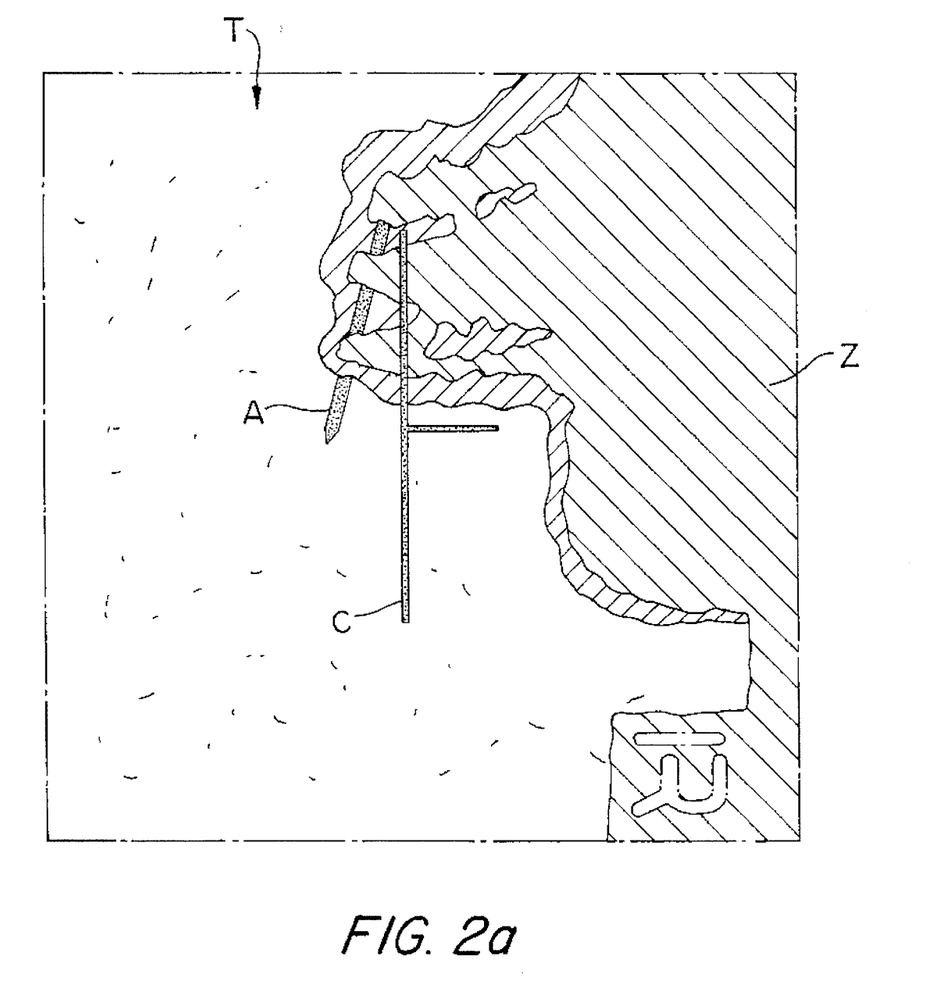
FIG. 2a is the unrefined image of an object of interest within its environment.

In the specific case of an unrefined image, FIG. 2a shows the projection A of the biopsy needled, a cross C whose center corresponds to the physical origin of the coordinates of the needle-carrier and which produces a dark area Z having variable intensity, and the tissues T forming the mammary gland of variable density, which creates a light area.

Figure 3A:
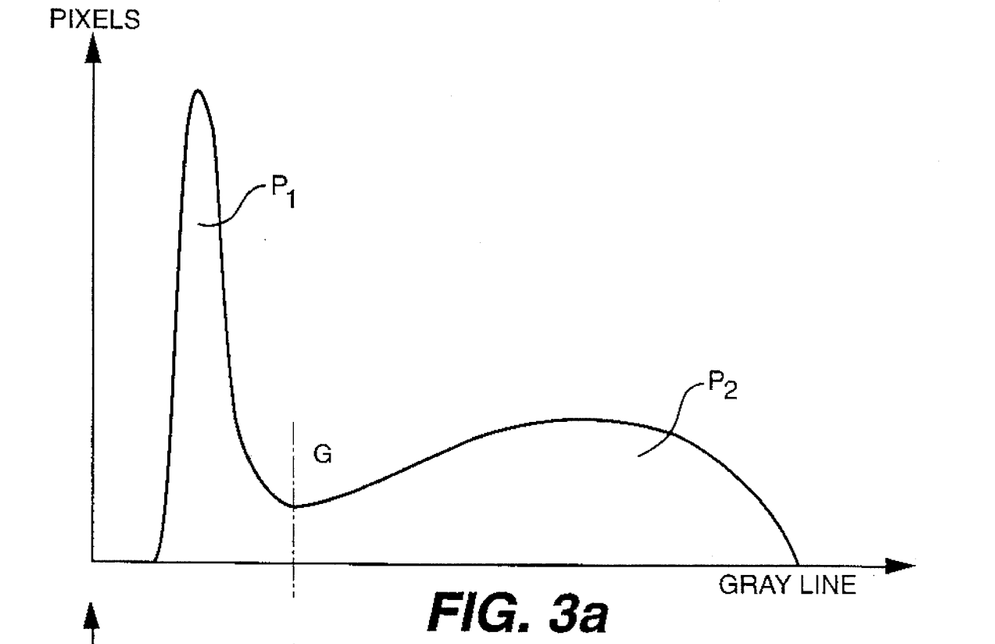
FIG. 3a is the histogram of the image.
Figure 3B:
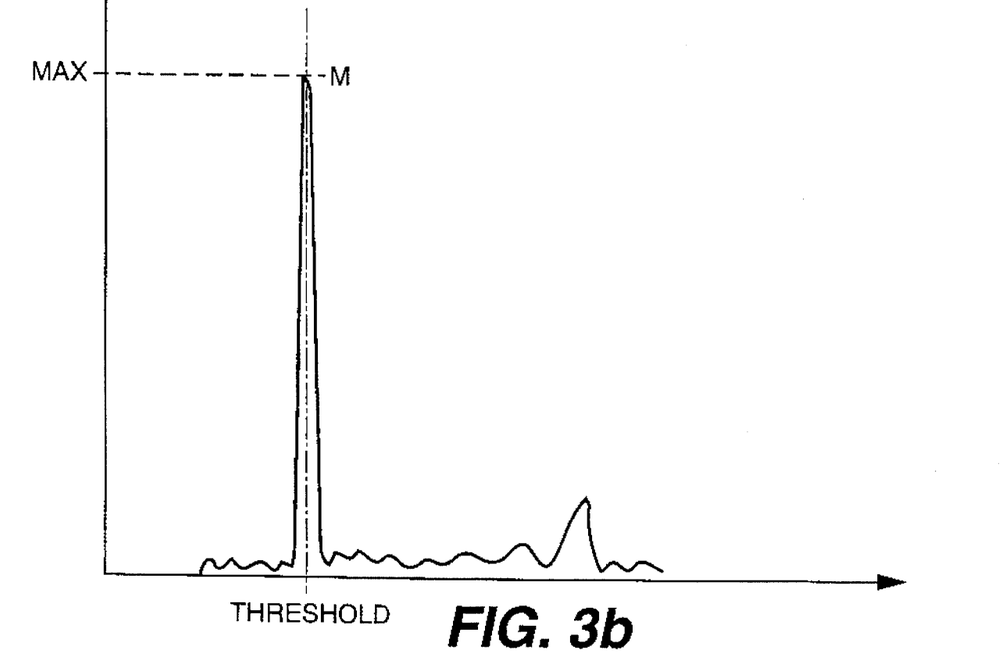
FIG. 3b illustrates the dynamics of the minima.

Parallel to step 0), the histogram of the image pixels will be analyzed during step 1 ) (illustrated in FIG. 3a). The gray level is shown along the abscissa, and the presence of the gray levels in pixels is shown along the ordinate. Peak $P_1$ corresponds to the high-contrast object, and peak $P_2$, to the tissues of the mammary gland. The position of the valley G separating these two peaks determines the threshold value allowing subsequent segmentation of the object encompassing the point of interest. For example, the position of the maximum M of the dynamics of the minima is selected as calculated for a certain range of gray levels, as shown in FIG. 3b.

Figure 2B:
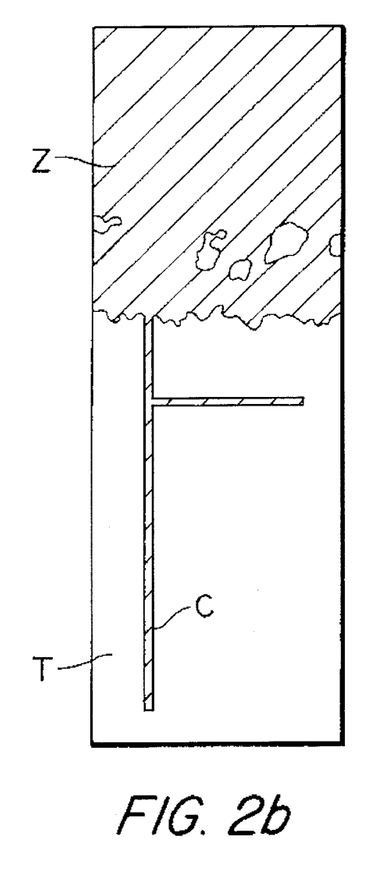
FIG. 2b is the unrefined area of interest for which a threshold has been determined.

Step 2 consists in determining the threshold of the image or area of interest delimited in Step 1, in order to obtain a binary image incorporating two gray levels (FIG. 2b). In this threshold-determined area of interest, the light portion corresponds for the most part to the mammary gland T, and the dark portion, to the high-contrast areas, including the needle-carrier.

Figures 2C, 2D:
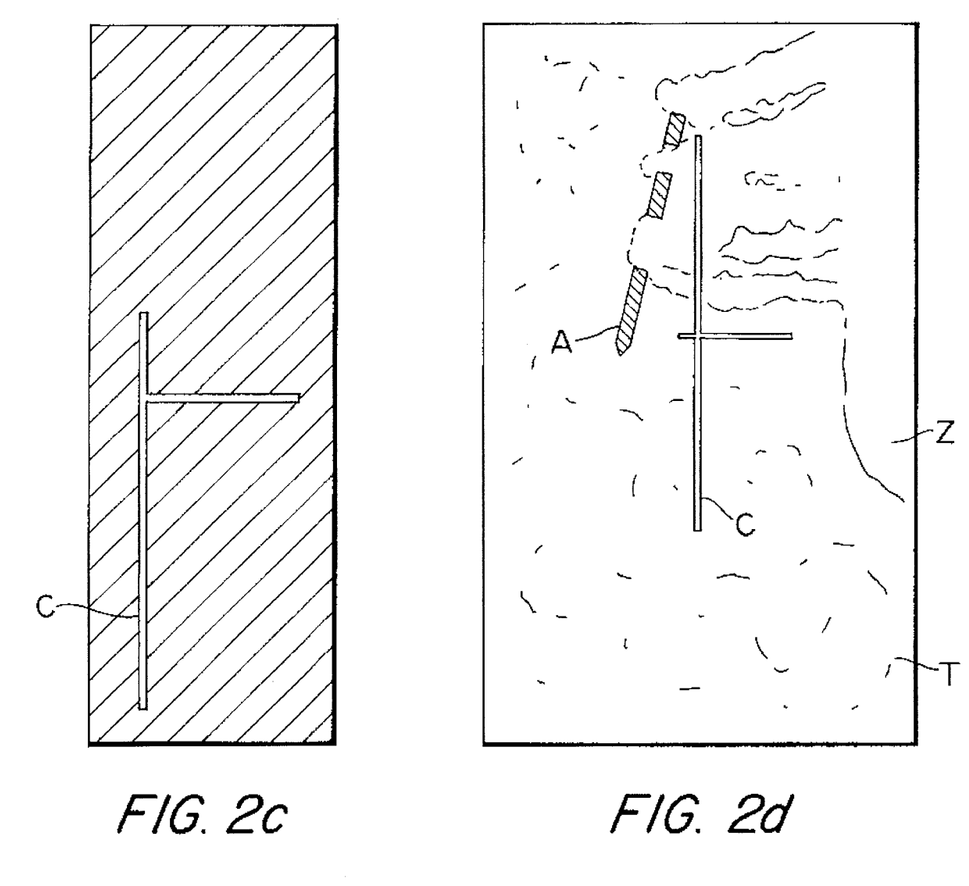
FIG. 2c is the projection of the segmented object of interest.
FIG. 2d indicates the location of the point of interest by a cursor.

Step 3 entails filtering to remove the structures not belonging to the projection of the object encompassing the point of reference. The filter used, whether linear or non-linear, is constructed as a function of the geometric characteristics of the object of interest, needle-carrier or needle, so as to preserve only the structure corresponding to the projection of the object in which the point of interest is located, as shown in FIG. 2c, on which the high-contrast object of interest appears as a light area and the surrounding tissues, as a dark one.

Finally, step 4 permits localization of the point of interest corresponding to the projection of the reference point within the plane of the image receiver when the projection of the object in which the reference point is found is segmented. Accordingly, the value of its coordinates are obtained in the image reference mark (FIG. 2d).

Figure 4:
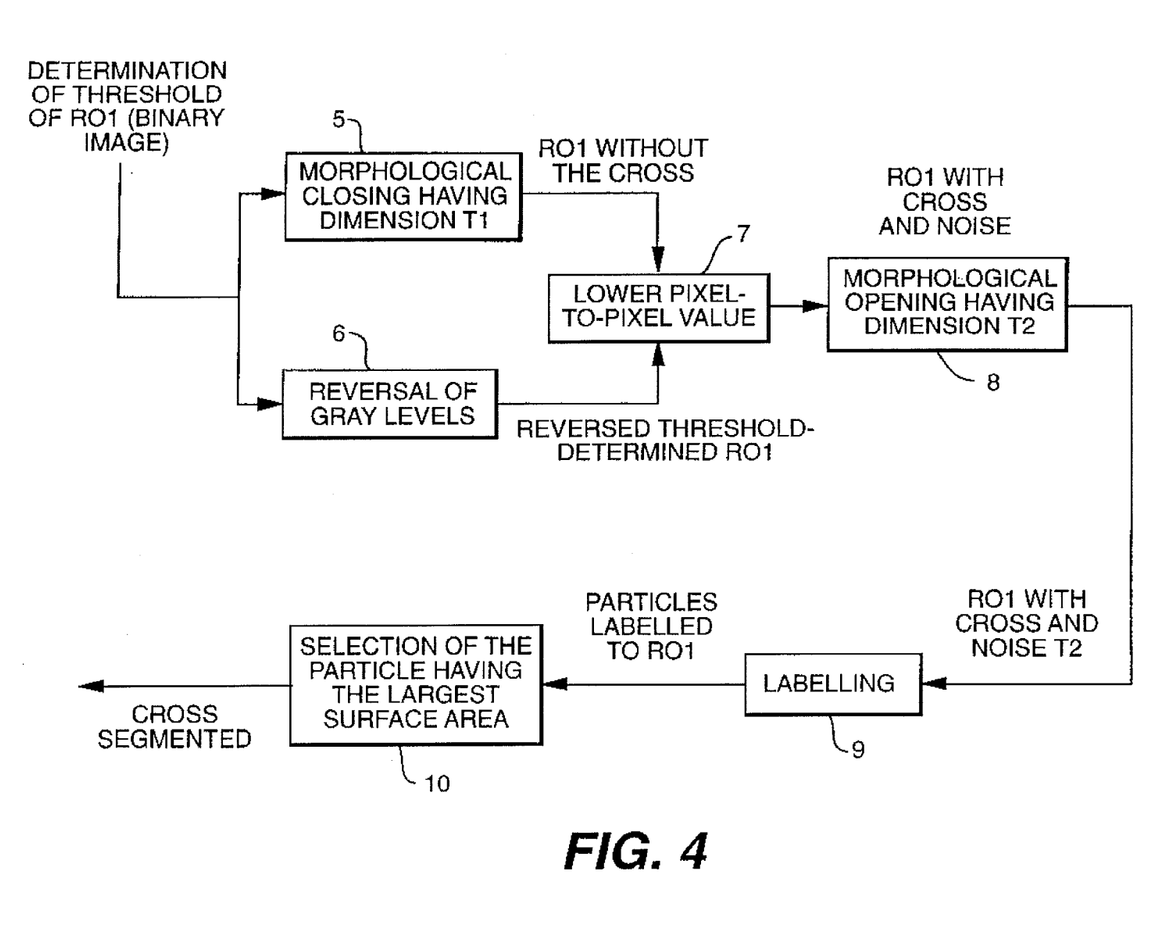
FIG. 4 shows an example of the establishment of the step involving filtering of the area of interest as part of the position-finding procedure according to the invention.

As a non-limiting example, step 3 involving filtering based on the morphological criteria of the object of interest is broken down into several steps, as shown in FIG. 4. In the example selected, filtering is performed based on morphological criteria specified in this way: it is assumed that the structures to be preserved are narrow and have a large surface area as compared with the surface area of the structures present in the area of interest within which the image analysis is carried out.

Figure 5A:
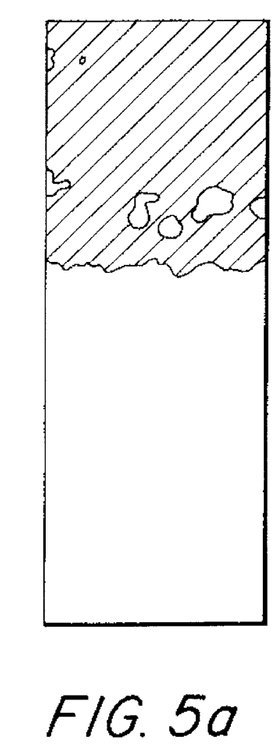
FIG. 5a shows the area of interest in the absence of the object of interest.

The filtering of the threshold-determined area of interest comprises a step 5 involving a morphological closure having a dimension $T_1$ intended to delete from the image all of the structures having a dimension smaller than $T_1$ and the same gray level, in particular the projection of the object of interest, i.e., the cross formed by the patient-support or the needle itself in the control procedure. The value of $T_1$ is chosen based on the a priori knowledge of the sizes of the structures one wishes to remove, either the cross or the needle. The result is illustrated in FIG. 5a, which shows the area of interest from which the cross has been removed.

Figure 5B:
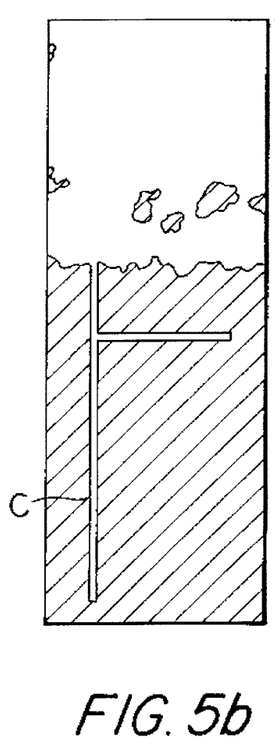
FIG. 5b shows the reversed area of interest for which a threshold has been determined.

Simultaneously, a step 6 consists in reversing the gray levels of an initial threshold-determined area of interest of the image or of the initial threshold-determined image. The areas which are dark at the outset, including the cross C as it appears in FIG. 2b, have become white in FIG. 5b.

Next, step 7 involves comparing the two images or areas of interest obtained during the preceding steps 5 and 6, and choosing for each pixel the lowest gray level between these two images. Step 7 is intended for preservation of only those structures having a dimension smaller than $T_1$, as shown in FIG. 5c, which shows the cross C formed by the patient support and the residual noise B.

Figure 5C:
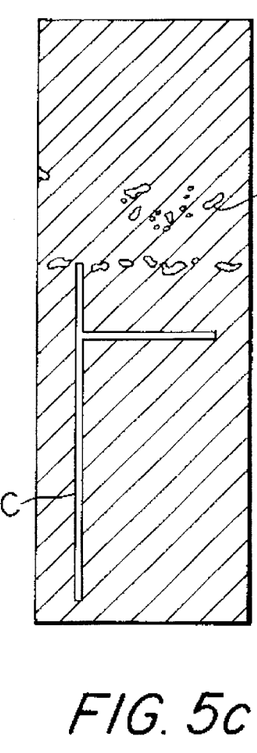
FIG. 5c illustrates the area of interest with the object of interest and residual noise.
Figure 5D:
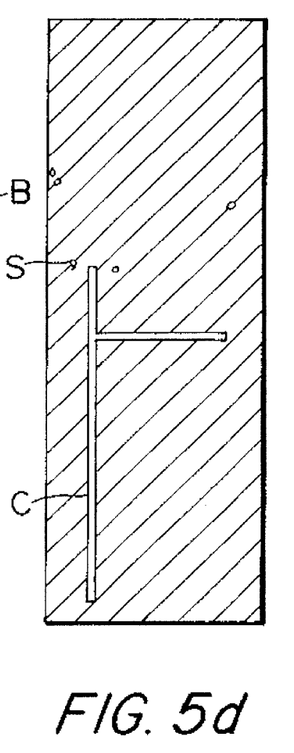
FIG. 5d shows the area of interest obtained following the step involving morphological opening of dimension T2 performed on the area in FIG. 5c.

The following step 8 is a morphological opening having dimension $T_2$, which is designed to delete the small structures having the same gray level as the object of interest, which is light in FIG. 5c and of a dimension smaller than $T_2$, these structures constituting the noise, so as to leave in the area of interest only the object of interest (in the case under consideration, the cross) and the structures S of a dimension greater than $T_2$, as shown in FIG. 5d. The value of $T_2$ is chosen based on the a priori knowledge of the size of the structures constituting the noise to be removed.

Figure 5E:
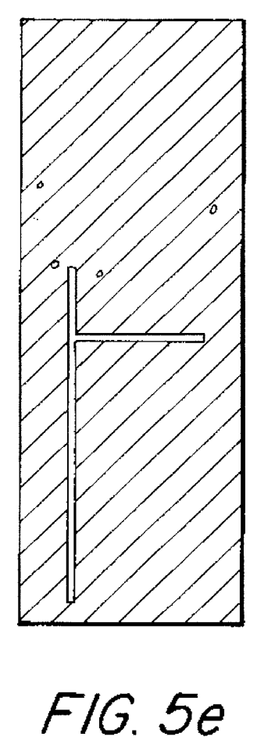
FIG. 5e is the area of interest after labelling.

These various structures remaining in the area of interest are labelled, i.e., processed individually, during step 9. Measures can be made of each of them and a numerical value assigned. In particular, it is possible to assign to each structure a gray level proportional to its surface area, as illustrated in FIG. 5e.

Finally, step 10 makes it possible to select the structure of the area of interest having the largest surface area, i.e., that corresponding to the projection of the object of interest to be segmented. FIG. 2c illustrates the cross corresponding to the segmented patient-support.

According to another feature of the invention, step 4 involving localization of the point of interest may, during the position-finding procedure according to the invention, take into consideration the specific geometric characteristics of the object on which the point of interest in located.

Figure 6:
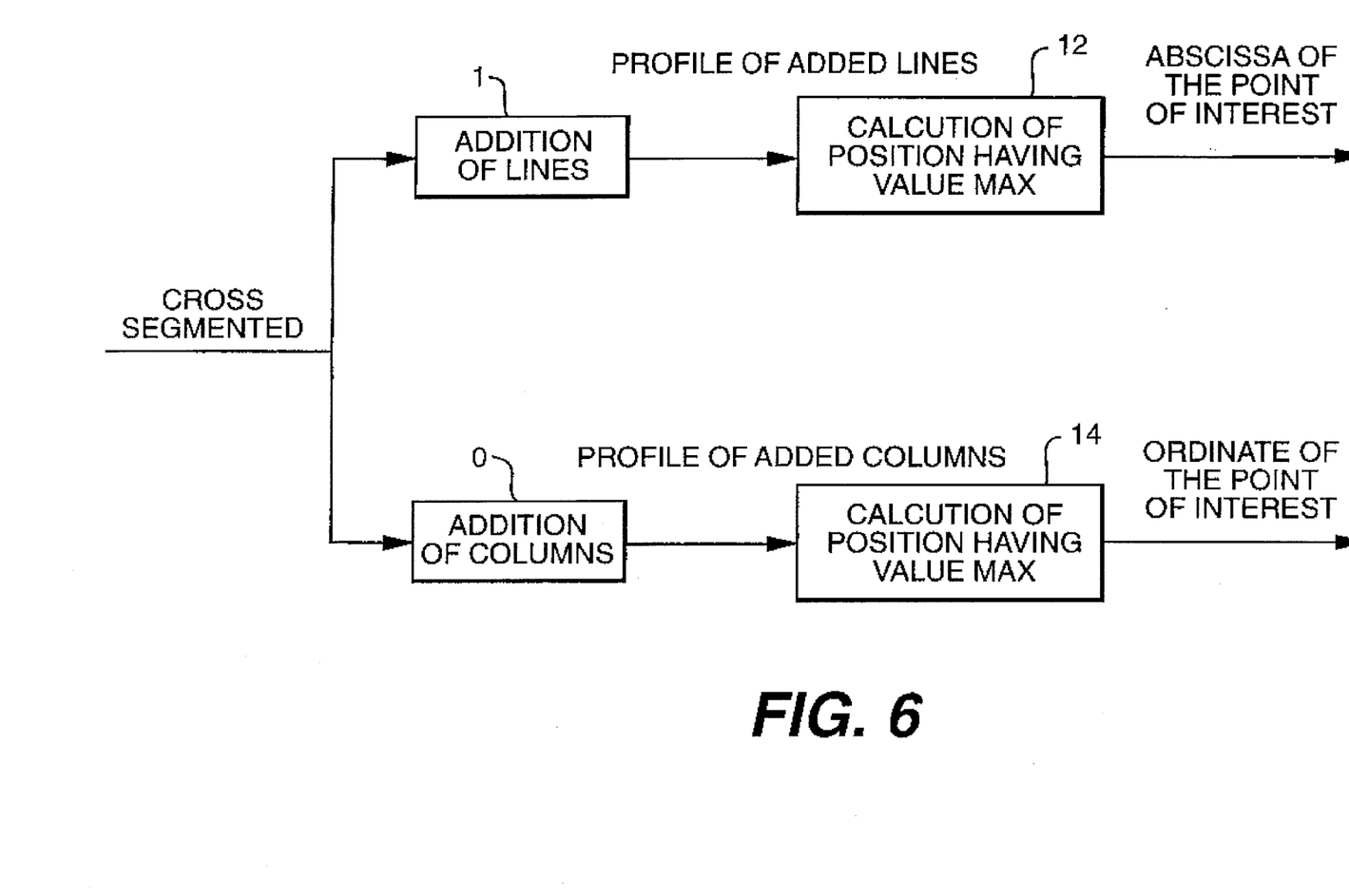
FIG. 6 is an example of the implantation of the step involving localization of the point of interest belonging to the position-finding procedure according to the invention.
Figure 7A:
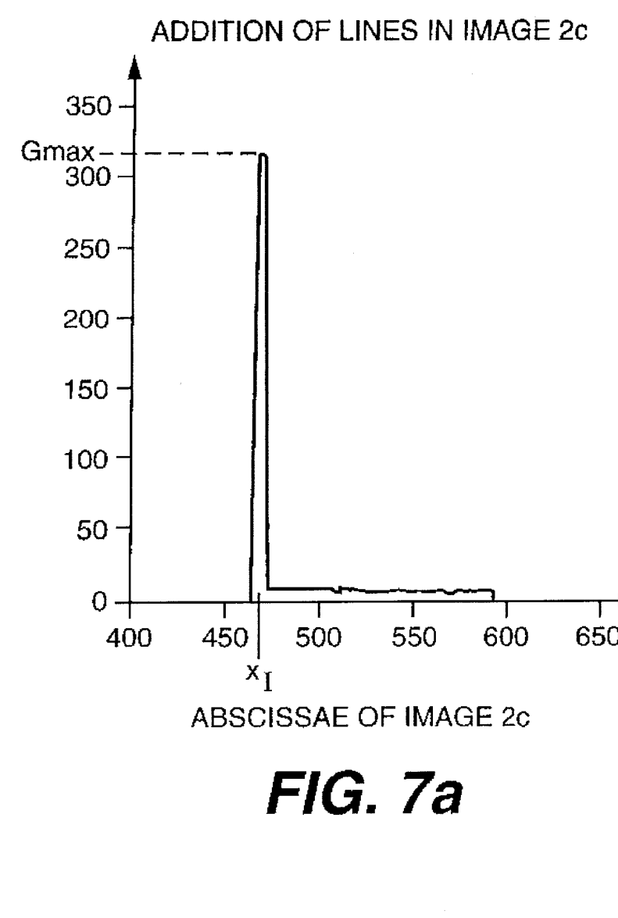
FIGS. 7a and 7b illustrate the contours of the added lines and columns of the image.
Figure 7B:
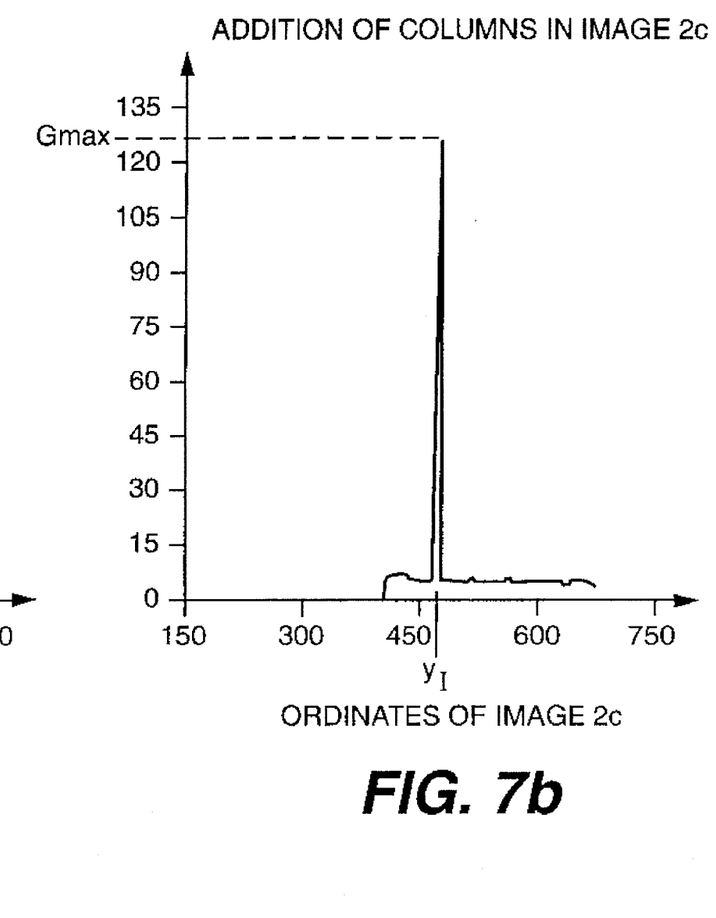

In the following non-limiting embodiment, it is assumed that the geometric reference mark of the patient-support is a cross having a non-null thickness whose arms are parallel or virtually parallel to the lines and columns of the image. In this case, step 4 comprises the following steps, as shown in FIG. 6:

a step 11 involving the addition of the lines delivering the profile of the added lines, as illustrated in FIG. 7a;

a step 12 involving calculation of the position of the maximum value Gmax of the gray levels along the X axis of the image, thus providing the abscissa $x_I$ of the point of interest in the reference mark of the image;

a step 13 involving summation of the columns providing the profile of the added columns (FIG. 7b);

a step 14 involving the calculation of the position of the maximum $G_{max}$ of the gray levels, thereby giving the ordinate $y_I$ of the point of interest in the reference mark of the image.

The automatic position-finding procedure according to the invention and used in stereotactic mammography examinations exhibits, as compared with present-day examinations, the advantage of reducing the number of required operations by the radiologist, and thus the number of possible errors, of decreasing the time required for mammograph, and of increasing patient comfort. It also makes possible the enhanced accuracy of the medical or surgical procedure accompany this examination and the determination of whether or not the biopsy needle has indeed reached its reference position.

We claim:

1. Procedure for automatic position-finding of a point of interest in an object exhibiting high contrast in relation to the surrounding tissues using a stereotactic photographic device delivering pairs of stereotactic images, each one composed of pixels with different gray levels which constitute a histogram of said images, said device including a digital image-acquisition system associated with algorithms for processing of these images, said procedure comprising, for each image belonging to the pair of stereotactic images, a step involving analysis of the histogram of the image pixels and a step involving filtering based on morphological criteria, wherein said procedure includes the following additional steps for each image belonging to the pair of stereotactic images:

1) determination of a threshold corresponding to the difference between the high-contrast object and the surrounding tissues, said determination being based on the analysis of the image histogram;

2) comparison between said image and said previously determined threshold in order to obtain a binary image incorporating two gray levels;

3) filtering of the threshold-determined image in the preceding step, based on the morphological criteria of the object in which the point of interest is located in order to obtain a segmented projection of said object;

4) localization of the point of interest in a reference mark of the image.

2. Position-finding procedure according to claim 1, wherein said procedure comprises an initial step in which the image is restricted to an area of interest delimited around the projection of the object encompassing the point of interest on each of the two images belonging to the pair of stereotactic images, based on the geometry of the acquisition system and the dimensions of the components of the stereotactic photographic device.

3. Position-finding procedure according to claim 1 or 2, the projection of the high-contrast object, in which the point of interest is located, having a width below the width of the structures present in the threshold-determined image and having a surface area superior to the surface of the said structures, wherein the step involving filtering of the threshold-determined image comprises the following steps:

5) morphological closure having dimension $T_1$ for deletion of all structures of the threshold-determined image having the same gray level as the object of interest and a dimension smaller than $T_1$;

6) inversion of the gray levels of the initial threshold-determined image;

7) comparison of the two images obtained during the two preceding steps and selection for each pixel of the lowest gray level between these two images;

8) morphological opening having dimension $T_2$ for deletion of the structures of the image having the same gray level as the object of interest and a dimension smaller than $T_2$;

9) labelling of the structures present in the image after the morphological opening, assigning to each structure a gray level proportional to its surface area;

10) selection of the structure having the largest surface area producing segmentation of the projection of the object containing the point of interest.

4. Position-finding procedure according to claim 1 or 2, the projection of the object containing the point of interest being a cross having a non-null thickness and whose two arms are parallel to the lines and columns of the image, wherein step 4) involving localization of the point of interest comprises the following steps:

11) summation of the lines of said segmented projection of said high-contrast object;

12) calculation of the position of the maximum value of the gray levels along the abscissa axis of the image, thus giving the abscissa of the point of interest in the image reference mark;

13) summation of the columns of said segmented projection of said high-contrast object;

14) calculation of the position of the maximum value of the gray levels along the ordinate axis of the image, thereby giving the ordinate of the point of interest of the image reference mark.

5. Position-finding procedure according to claim 1, wherein the value of the threshold as determined during step 1) involving analysis of the histogram of the image corresponds to the position of a minimum (G) of the histogram separating a first maximum ($P_1$) characteristic of the high-contrast objects of interest from a second maximum ($P_2$) characterizing the surround tissues.

6. Position-finding procedure according to claim 5, wherein the value of the threshold as determined during step 1) is the position of a maximum of the dynamics of the minima as calculated for a given range of gray levels.

* * * * *